United States Patent [19]
Shuldiner et al.

[11] Patent Number: 5,877,283
[45] Date of Patent: Mar. 2, 1999

[54] POLYPEPTIDE FOR OBESITY AND TYPE II DIABETES MELLITUS

[75] Inventors: Alan R. Shuldiner, Columbia; Jeremy Walston, Baltimore; Kristi Silver, Baltimore; Jesse Roth, Baltimore, all of Md.

[73] Assignee: The Johns Hopkins University School of Medicine, Baltimore, Md.

[21] Appl. No.: 97,562

[22] Filed: Jun. 15, 1998

Related U.S. Application Data

[62] Division of Ser. No. 446,530, May 19, 1995, Pat. No. 5,766,851.

[51] Int. Cl.⁶ ............................................... C07K 14/435
[52] U.S. Cl. ..................... 530/350; 530/395; 530/827; 536/23.5
[58] Field of Search ................................ 530/395, 350, 530/827; 536/23.5

[56] References Cited

U.S. PATENT DOCUMENTS 5,288,607  2/1994  Emorine et al. ........................ 435/6

FOREIGN PATENT DOCUMENTS 9402590  2/1994  WIPO .

OTHER PUBLICATIONS

Lelias et al., *Molecular cloning of a human β3–adrenergic receptor cDNA*, Febs Letters, 324(2):127, 1993.

*Primary Examiner*—Carla J. Myers
*Attorney, Agent, or Firm*—Fish & Richardson P.C.

[57] ABSTRACT

The present invention provides a novel polypeptide characterized by a non-conservative missense mutation, Trp64Arg, in the β3-adrenergic receptor (β3AR) that increases susceptibility to obesity and non-insulin dependent diabetes mellitus (NIDDM; type II diabetes). Also provided are methods of diagnosis and methods of treatment of subjects having or at risk of having type II diabetes/obesity.

1 Claim, 3 Drawing Sheets

POLYPEPTIDE FOR OBESITY AND TYPE II DIABETES MELLITUS

This is a divisional of U.S. application Ser. No. 08/446,530, filed May 19, 1995, issuing on Jun. 16, 1998 as U.S. Pat. No. 5,766,851.

BACKGROUND OF THE INVENTION

1. Field of the Invention

This invention relates generally to non-insulin dependent diabetes mellitus (NIDDM) (type II) and obesity, and specifically to a novel Trp64Arg mutation in the β3-adrenergic receptor that increases susceptibility to obesity and type II diabetes.

2. Description of Related Art

Non-insulin dependent diabetes mellitus (NIDDM) is one of the most common inherited diseases in man with an estimated prevalence in Caucasian populations of 8–10% (Harris, et al., *Diabetes*, 36:523–534, 1987). Although most forms of NIDDM do not exhibit simple Mendelian inheritance, the contribution of heredity is well recognized (Rotter, et al., *Diabetes Mellitus: Theory and Practice*, 378–413, 1990). The genetic basis of a few rare monogenic syndromes of NIDDM have been elucidated, but together, these syndromes account for a very small minority of cases (Taylor, et al., *Endocrine Rev.*, 13:566–595, 1992; Froguel, et al., *N. Engl. J. Med.*, 328:697–702, 1993; Steiner, et al., *Diabetes Care*, 13:600–609, 1990; and Kadowaki, et al., *N. Engl. J. Med.*, 330:962–968, 1994). It is likely that the common forms of NIDDM are complex and heterogenous, and result when a pool of mutant genes, each of which contributes modestly and in a subtle way, interact with each other and with environmental, aging and behavioral influences to lead to the expression of the disease. This pool of genes may vary between populations and among individuals within a population, despite the illusion of a clinically homogenous phenotype.

Obesity is a known risk factor for the development of NIDDM (Barrett-Conner, E., *Epidemiol. Rev.*, 11:172–181, 1989; and Knowler, et al.,*Am. J. Clin. Nutr.*, 53:1543–1551, 1991), and although less well studied than NIDDM, also has clear genetic determinants (Bouchard, C., *World Rev. Nutr. Diet*, 72:68–77, 1993; and Stunkard, et al., *N. Engl. J. Med.*, 314:193–197,1986). Potential candidate genes for obesity (and therefore also NIDDM) include those that influence energy expenditure. In adult Pima Indians, resting metabolic rate (RMR) is familial (Bogardus, et al., *N. Engl. J Med*, 315:96–100, 1986 ), and in prospective studies, a low RMR is a risk factor for weight gain and obesity (Ravussin, et al., *N. Engl. J Med*, 318:467–472, 1988). Studies in other populations (Bouchard, et al., *Metabolism*, 38:364–370, 1989; and Griffith, et al.,*Lancet*, 336:76–78, 1990), as well as in animal models (Coleman, D. L., *Diabetes*, 31:1–6, 1992), support the relationship between heredity, low RMR and obesity. In rodents, RMR is regulated by the sympathetic nervous system and acts through modulation of thermogenesis in brown adipose tissue (Lowell, et al., *Nature*, 366:740–749, 1993). Although humans do not have anatomically distinct deposits of brown adipose tissue, the identification of human uncoupling protein, a molecular marker widely regarded as being specific for brown adipose tissue, suggests that modulation of thermogenesis in adipose tissue may also be important in humans (Cassard, et al., *J. Cell Biochem.*, 43:255–264, 1990).

Obesity represents a primary health concern amongst industrialized countries. Studies on twins, adopted children and on animal models of obesity have shown that genetic factors are implicated in the dynamics of gaining weight (Bouchard, C., Perusse, L., *Ann. Rev. Nutr.*, 8:259–277, 1988). Morbid obesity in humans appears to have a particularly strong genetic component (Price, et al.,*Hum. Biol.*, 62:, 1990; and Adams, et al., *Obes. Res.*, 1:261–270, 1993). However, the molecular basis of inheritance of obesity in humans is unknown. Obesity results from an imbalance between caloric intake and energy expenditure. As adipose tissue plays a crucial role in the regulation of energy storage and mobilization, it has been the focus for studies involved in the identification of candidate genes. Recently, positional cloning approaches have succeeded in identifying an obesity gene in a monogenic rodent model, the ob mouse (Zhang, et al., *Nature*, 372:425–432, 1994). The human ob homologue has been cloned, but mutations, deletions, or polymorphisms in this gene have yet to be identified. In humans, evidence supports the involvement of several genes as well as environmental and behavioral influences in the predisposition, onset and progression of obesity and NIDDM.

The recent localization of the $\beta_3$-adrenergic receptor (β3AR) in adipose tissue (Emorine, et al., *Science*, 245:1118–1121, 1989; Spronsen, et al., *Eur. J. Biochem.*, 213:1117–1124, 1993; and Krief, et al., *J. Clin. Invest.*, 91:344–349, 1993) has spurred great interest in its potential role in the regulation of energy expenditure. Evidence in support of a role for the β3AR in the development of obesity and NIDDM include: i) β3AR expression is markedly decreased in rodent models of obesity (Collins, et al., *Mol. Endocrinol.*, 8:518–527, 1994; and Muzzin, et al., *J. Biol Chem.*, 266:24053–24058, 1991); ii) β3AR gene knock-out mice have a marked reduction in β-agonist stimulated lipolysis; iii) insulin downregulates ⊖3AR expression in vitro with a concomitant decrease in lipolysis and increase in lipogenesis (Feve, et al., *Proc. Natl. Acad. Sci*, 91:5677–5681, 1994); and iv) $\beta_3$-specific agonists have potent antiobesity and antidiabetic effects in both animals (Hims-Hagen, et al., *Am. J. Physiol*, 266:R1371–1382, 1994; and Connacher, et al., *Am. J. Clin. Nutr.*, 55:258S–261S, 1992) and humans (Mitchell, et al., *Int. J. Obes.*, 13:757–766, 1989).

There is a need to identify genes and defects in those genes that are directly related to obesity and diabetes. Such genes are useful as molecular markers for the early detection of susceptible individuals so that intervention regimes may be instituted for delay or prevention of obesity/diabetes disorders. A delay in the onset of diabetes would markedly reduce morbidity and mortality due to chronic complications. Further, identification of specific susceptibility genes would allow for the design of more effective medications having specific molecular targets.

SUMMARY OF THE INVENTION

The present invention is based on the discovery of a nonconservative missense mutation in the β3-adrenergic receptor (β3AR) which is associated with susceptibility to and development of non-insulin dependent diabetes mellitus (NIDDM, type II diabetes) and obesity. Now that the present invention defines the mutation at codon 64, $\underline{T}GG^{Trp} \rightarrow \underline{C}GG^{Arg}$ (Trp64Arg), which occurs in populations at increased risk for obesity and type II diabetes, more accurate diagnostic, prognostic, preventative and therapeutic regimes can be employed in individuals heterozygous or homozygous for the mutation.

The invention provides isolated oligonucleotide primers useful for diagnosis of a subject having or at risk of having type II diabetes and/or obesity. The invention also provides a method for diagnosis of such a patient comprising contacting target nucleic acid of a sample from the patient with a reagent that detects a mutation in the β3AR and detecting the mutation. In a preferred embodiment, the mutation described herein is identified by allele specific oligonucleotide hybridization or by restriction endonuclease digestion with an enzyme which specifically recognizes and cleaves the sequence including and flanking codon 64.

BRIEF DESCRIPTION OF THE DRAWINGS

FIG. 2 shows, in panel A, SSCP of segment 4 of the β3AR gene in 7 (of 10) diabetic Pima Indians. The arrow shows a variant pattern in lanes 2 through 6. Panel B shows direct dideoxy sequence analysis of PCR fragment 4 of the β3AR gene. The normal ($Trp^{64}$) sequence is shown on the left. Sequencing of one of the PCR products that gave an aberrant SSCP pattern shown on the right revealed both a thymidine (T) and cytosine (C) at nucleotide position 190; the patient was heterozygous for the nucleotide substitution which alters the predicted amino acid sequence at codon 64 ($TGG^{Trp} \rightarrow \underline{C}GG^{Arg}$; Trp64Arg).

DETAILED DESCRIPTION OF THE INVENTION

The present invention is based on the discovery of a point mutation in the β3- adrenergic receptor (β3AR) gene which occurs frequently in subjects having or at risk of having type II diabetes (NIDDM) and associated obesity. This finding provides genetic evidence that the mutation increases susceptibility to obesity and NIDDM, possibly through dysregulation of energy expenditure. The increased mortality at a younger age in subjects homozygous for the mutation is likely due to the earlier onset of diabetes (and thus complications associated with diabetes) as well as increased cardiovascular risk due to obesity.

A nonconservative missense mutation was identified in the first intracellular loop of the β3AR(codon 64 $TGG^{Trp} \rightarrow \underline{C}GG^{Arg}$; Trp64Arg). This missense mutation occurs with an allele frequency of 0.31 in Pima Indians, 0.13 in Mexican Americans, 0.12 in African Americans and 0.08 in Caucasian Americans. In Pimas, the mean age of onset of NIDDM was significantly earlier in subjects with the mutation (mean±SD =35.9±10.2 years in Trp64Arg homozygotes, 40.2±10.2 in Trp64Arg heterozygotes, and 40.9±10.7 in normal homozygotes; p=0.022). After adjustment for fat free mass, fat mass, and gender, Trp64Arg homozygotes (n=22) expended an average of 82 kcal/day less than normal homozygotes (n=82); Trp64Arg heterozygotes (n=106) were intermediate with an average RMR 35.7 kcal/day less than normal homozygotes (p=0.14; overall significance for regression). There was a trend towards increased body mass index (BMI) in subjects with the mutation (mean±SD=35.2±8.0 kg/m² in Trp64Arg homozygotes, 34.1±7.9 in Trp64Arg heterozygotes, and 33.9±7.5 in normal homozygotes). Pima subjects with the Trp64Arg β3AR missense mutation have a significantly earlier onset of NIDDM, and tend to have lower RMR and increased BMI. This mutation may accelerate the onset of NIDDM by altering the balance of energy metabolism. In a first embodiment, the present invention provides isolated oligonucleotide primer(s) for diagnosis of a subject having or at risk of having type II diabetes mellitus and/or obesity, wherein the primer hybridizes with a target polynucleotide sequence having substantially the sequence selected from the group consisting of:

5'-GTGTTGGCCGTATTGGGCG-3' (SEQ ID NO:1) and
5'-GGTGATGGGACTCCTGGTGG-3' (SEQ ID NO:2)
and sequences substantially complementary thereto.
These unique oligonucleotide primers were produced based upon identification of regions within the β3AR locus. The term "sequences substantially complementary thereto" or "substantially the sequence" refers to sequences which hybridize to the sequences provided (e.g., SEQ ID NO:1 and SEQ ID NO:2) under stringent conditions and/or sequences having sufficient homology with SEQ ID NO:1 and SEQ ID NO:2, such that the oligonucleotide primers of the invention hybridize to the sequence. The term "isolated" as used herein includes oligonucleotides substantially free of other nucleic acids, proteins, lipids, carbohydrates or other materials with which they may be naturally associated. A "target polynucleotide" refers to the nucleic acid sequence of interest, e.g., the β3AR encoding polynucleotide. Other target nucleotide sequences within the β3AR locus and other primers which can be used for primer hybridization will be known or readily ascertained to those of skill in the art.

Preferably, the primers of the invention which hybridize to the upstream and downstream sequences of the β3AR gene have the sequence:

5'-CGCCCAATACCGCCAACAC-3' (SEQ ID NO:3) or
5'-CCACCAGGAGTCCCATCACC-3' (SEQ ID NO:4).
The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA Polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the polymorphic locus. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et al. (*Molecular Cloning: A Laboratory Manual*, Cold Spring Harbor, N.Y., pp 280, 281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation), such as Taq polymerase. Suitable enzymes will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion.

The amplified product may be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al, *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Preferably, the method of amplifying is by PCR, as described herein and as is commonly used by those of ordinary skill in the art. Alternative methods of amplification have been described and can also be employed as long as the β3AR locus amplified by PCR using the primers of the invention is similarly amplified by the alternative means. Such alternative amplification systems include but are not limited to self-sustained sequence replication, 3SR, which begins with a short sequence of RNA of interest and a T7 promoter. Reverse transcriptase copies the RNA into cDNA and degrades the RNA, followed by reverse transcriptase polymerizing a second strand of DNA. Another method nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$-fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair. Nucleic acid amplification by strand displacement activation (SDA) utilizes a short primer containing a recognition site for HincII with a short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented temperature cycling. Another amplification system useful in the method of the invention is the QB Replicase System. Although PCR is the preferred method of amplification of the invention, these other methods can also be used to amplify the β3AR locus as described in the method of the invention.

In another embodiment, the invention provides an isolated polypeptide having an amino acid sequence of a β3-adrenergic receptor having a substitution of tryptophan at amino acid residue 64 with arginine and wherein the substituted receptor is associated with type II diabetes mellitus and/or obesity. The term "isolated" as used herein includes the polypeptide substantially free of other proteins, lipids, carbohydrates and other materials with which it is naturally associated.

The invention also includes an isolated polynucleotide encoding a polypeptide having an amino acid sequence of a β3-adrenergic receptor having a substitution of tryptophan at amino acid residue 64 with arginine and wherein the substituted receptor is associated with type II diabetes mellitus and/or obesity. The polynucleotide include DNA, cDNA and RNA sequences which encode a β3AR polypeptide having the mutation as described herein. Alternatively, one of skill in the art would know standard techniques to isolate the wild-type β3AR gene and create a mutation as described, by site-directed mutagenesis, for example. The codon, TGG at codon 64 may be replaced by CGG, thereby creating the non-conservative missense mutation described herein.

It is understood that all polynucleotides encoding all or a portion of β3AR or Trp64Arg β3AR are also included herein, as long as they encode a polypeptide with β3AR or Trp64Arg β3AR activity. Such polynucleotides include naturally occurring, synthetic, and intentionally manipulated polynucleotides. For example, as described above, wild-type β3AR polynucleotide may be subjected to site-directed mutagenesis as stated above. The polynucleotide sequence for β3AR or Trp64Arg β3AR also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of Trp64Arg β3AR polypeptide encoded by the nucleotide sequence is functionally unchanged.

Minor modifications of the Trp64Arg β3AR primary amino acid sequence may result in proteins which have substantially equivalent activity as compared to the Trp64Arg β3AR polypeptide described herein. Such modifications may be deliberate, as by site-directed mutagenesis, or may be spontaneous. All of the polypeptides produced by these modifications are included herein as long as the biological activity of Trp64Arg β3AR still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for Trp64Arg β3AR biological activity.

The nucleotide sequence encoding the β3AR polypeptide of the invention includes the wild-type receptor polypeptide having an arginine at codon 64 substituted for tryptophan (as above), and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the Trp64Arg β3AR polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981; Maniatis, et al, *Molecular Cloning: A Laboratory Manual*, Cold Spring Harbor, N.Y. 1989).

The development of specific DNA sequences encoding Trp64Arg β3AR can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the Trp64Arg β3AR of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial or baculovirus expressed polypeptide, or fragments thereof, provided by the invention, may be carried out by conventional means including preparative chromatography and immunological separations involving monoclonal or polyclonal antibodies.

The polypeptides of the invention can also be used to produce antibodies which are immunoreactive or bind to epitopes of the Trp64Arg β3AR polypeptides. While antibodies to β3AR, may be useful for production of antibodies, it is desirable to utilize the missense mutation protein (Trp64Arg) to produce novel antibodies. While not wanting to be bound by a particular theory, the truncated protein may form additional conformational epitopes which are not present in wild-type β3AR polypeptide, therefore, Trp64Arg β3AR-specific antibodies are produced.

Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature,* 256:495, 1975; *Current Protocols in Molecular Biology*, Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the Trp64Arg β3AR polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

In another embodiment, the invention provides a method for diagnosis of a subject having or at risk of having type II diabetes mellitus and/or obesity comprising contacting a target nucleic acid of a sample from the subject with a reagent that detects a mutation in the β3AR gene and detecting the mutation. The method of diagnosis is useful not only for individuals having a type II diabetes/obesity disorder, but also for those individuals at risk of developing type II diabetes/obesity in the future. For example, a more accurate diagnosis can be made based on a finding of heterozygosity or homozygosity for the mutation. Those being normal homozygotes, heterozygotes and homozygotes for the mutation will have increasing susceptibility to developing type II diabetes/obesity and associated complications, respectively.

The invention provides a method for diagnosis of a subject having or at risk of having type II diabetes and/or obesity, and complications associated therewith, comprising contacting an anti-Trp64Arg β3AR antibody or nucleic acid probe with a cell suspected of having a Trp64Arg β3AR associated disorder and detecting binding to the antibody or nucleic acid probe. For purposes of the invention, an antibody or nucleic acid probe specific for Trp64Arg β3AR may be used to detect and/or to bind to Trp64Arg β3AR polypeptide (using antibody) or polynucleotide (using nucleic acid probe) in biological fluids or tissues. Any sample containing a detectable amount of Trp64Arg β3AR protein, RNA or DNA can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis. Preferably, the sample is blood.

The antibody reactive with Trp64Arg β3AR or the nucleic acid probe is preferably labeled with a compound which allows detection and quantitation of binding to Trp64Arg β3AR. Any specimen containing a detectable amount of antigen or polynucleotide can be used. The level of Trp64Arg β3AR in the suspect cell can be compared with the level in a normal cell or the nature of the transcript or gene product can be compared with a normal cell, in order to determine whether the subject has a Trp64Arg β3AR associated disorder. Preferably the subject is human.

Preferably, the method for diagnosis of a subject having or at risk of having type II diabetes mellitus and/or obesity, including complications associated therewith, comprises contacting a target nucleic acid of a sample from the subject with a nucleic acid probe that detects a mutation in the β3AR gene and detecting the mutation. A nucleic acid probe specific for detection of the codon 64 mutation, e.g., TGG to CGG, is contacted with a target nucleic acid from a cell of a subject either suspected of having a β3AR associated disorder or from a subject at risk for the disorder, and detecting binding to the nucleic acid probe. The nucleic acid probe is preferably labeled with a compound which allows detection and quantitation of binding to codon 64 and nucleotides flanking the codon. Any specimen containing a detectable amount of polynucleotide can be used. Preferably the subject is human.

When the cell component is nucleic acid, it may be necessary to amplify the nucleic acid prior to binding with a β3AR probe specific for the mutation described herein. Preferably, polymerase chain reaction (PCR) is used, however, other nucleic acid amplification procedures such as ligase chain reaction (LCR), ligated activated transcription (LAT), QB replicase, and nucleic acid sequence-based amplification (NASBA) may be used as described above.

Preferably, the target nucleic acid for diagnosis of a subject having or at risk of having a type II diabetes/obesity disorder has a nucleotide sequence selected from 5'-TCGGAGTCCAGGCGATG-3' (SEQ ID NO:5) and 5'-TCGGAGTCCGGGCGATG-3' (SEQ ID NO:6) or sequences substantially complementary thereto. The position of the point mutations at codon 64 are underlined. Those of skill in the art can design appropriate allele specific oligonucleotides for identification of such a mutation. For example, preferably the probes have substantially the sequence 5'-CATCGCCTGGACTCCGA-3' (SEQ ID NO:7) or 5'-CATCGCCCGGACTCCGA-3' (SEQ ID NO:8) or sequences substantially complementary thereto.

In addition, the method of diagnosis described herein can be performed by contacting the β3AR target nucleic acid with a restriction endonuclease which specifically recognizes a sequence located within and/or flanking, codon 64. The nucleic acid is treated with such a restriction endonuclease and the product(s) are detected by gel electrophoresis or Southern blot analysis, for example. Preferably, the restriction endonuclease recognizes and cleaves a nucleic acid having a sequence CC↓(A/T)GG. Such restriction endonucleases include BstNI, BstOI, ApyI, EcoRII or MvaI, used alone or in combination. Other restriction endonucleases capable of recognizing and cleaving the sequence including the point mutation in β3AR will be known to those of skill in the art.

The present invention identifies a nucleotide sequence that can be expressed in an altered manner as compared to expression in a normal cell, therefore it is possible to design appropriate therapeutic or diagnostic techniques directed to this sequence. Detection of levels of Trp64Arg β3AR expression is accomplished by hybridization of nucleic acids isolated from a cell suspected of having a Trp64Arg β3AR associated disorder with a Trp64Arg β3AR polynucleotide of the invention. Techniques commonly used in the art, for example, Northern Blot analysis, PCR RT-PCR, or RNase protection assays, are utilized to quantitate expression of Trp64Arg β3AR. Other standard nucleic acid detection techniques will be known to those of skill in the art.

Treatment of a β3AR associated disorder wherein codon 64 contains a missense mutation includes modulation of the β3 adrenergic receptor through the use of β-agonist therapy. The term "modulate" envisions the suppression of expression or activity of mutated β3AR when it is over-expressed or over-active, or augmentation of β3AR activity or expression when it is under-expressed or underactive. The nucleic acid approach utilizes, for example, antisense nucleic acid, ribozymes, or triplex agents to block transcription or translation of the mRNA having the mutation at codon 64, either by masking that mRNA with an antisense nucleic acid or triplex agent, or by cleaving it with a ribozyme.

Beta-receptor agonists include isoproterenol, epinephrine, norepinephrine, dobutamine, phenylephrine, terbutaline, albuterol, isoethareine, metaproterenol, pirbuteral and ritodrine, for example. Other effective beta-receptor agonists will be known to those of skill in the art.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Alternatively, antisense may accelerate mRNA degradation. Antisense oligomers of about 15 nucleotides are preferred, since they are easily synthesized and are less likely to cause problems than larger molecules when introduced into the target Trp64Argβ3AR-producing cell. The use of antisense methods to inhibit the in vitro translation of genes or decrease RNA stability, is well known in the art (Marcus-Sakura, Anal.Biochem., 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.,* 1(3):227, 1991; Helene, C., *Anticancer Drug Design,* 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

The present invention also provides gene therapy for the treatment of a subject having or at risk of having type II diabetes and/or obesity related thereto, comprising introducing into the cells of a host subject, an expression vector comprising a polynucleotide sequence encoding β3-adrenergic receptor, wherein the cell expresses a therapeutically effective amount of the β3-adrenergic receptor.

The polynucleotide is introduced by an expression vector introduced into the cells of the host subject, in vitro, and the transformed cells are reintroduced into the subject. Such therapy would achieve its therapeutic effect by introduction of the missense mutation antisense polynucleotide into cells of the subject having the disorder. Alternatively, it may be desirable to introduce polynucleotides encoding full length wild-type β3AR. Delivery of antisense polynucleotide or wild-type β3AR polynucleotide, can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a β3AR sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing β3AR, e.g., the missense mutation β3AR antisense polynucleotide or sense wild-type β3AR polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to $\psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for missense Trp64Arg β3AR antisense polynucleotides or wild-type β3AR polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macro-molecules. RNA, DNA and intact virions can be encapsulated within the aqueous interior and be delivered to cells in a biologically active form (Fraley, et al, *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The materials for use in the method of the invention are ideally suited for the preparation of a diagnostic kit. Such a kit may comprise a carrier means being compartmentalized to receive in close confinement one or more container means such as vials, tubes, and the like, each of the container means comprising one of the separate elements to be used in the method. For example, one of the container means may comprise means for amplifying β3AR DNA, said means comprising the necessary enzyme(s) and oligonucleotide primers for amplifying said target DNA from the subject. The oligonucleotide primers include primers having a sequence:

5'-CGCCCAATACCGCCAACAC-3' (SEQ ID NO:3) or

5'-CCACCAGGAGTCCCATCACC-3' (SEQ ID NO:4)

or primer sequences substantially complementary or substantially homologous thereto. The target flanking 5' and 3' polynucleotide sequence has substantially the sequence selected from the group consisting of:

5'-GTGTTGGCCGTATTGGGCG-3' (SEQ ID NO:1) and

5'-GGTGATGGGACTCCTGGTGG-3' (SEQ ID NO:2) and sequences substantially complementary or homologous thereto.

Other oligonucleotide primers useful for amplifying β3AR will be known or readily ascertainable to those of skill in the art.

Although the invention has been described with reference to the presently preferred embodiment, it should be understood that various modifications can be made without departing from the spirit of the invention. Accordingly, the invention is limited only by the following claims.

EXAMPLES

Figure 1:
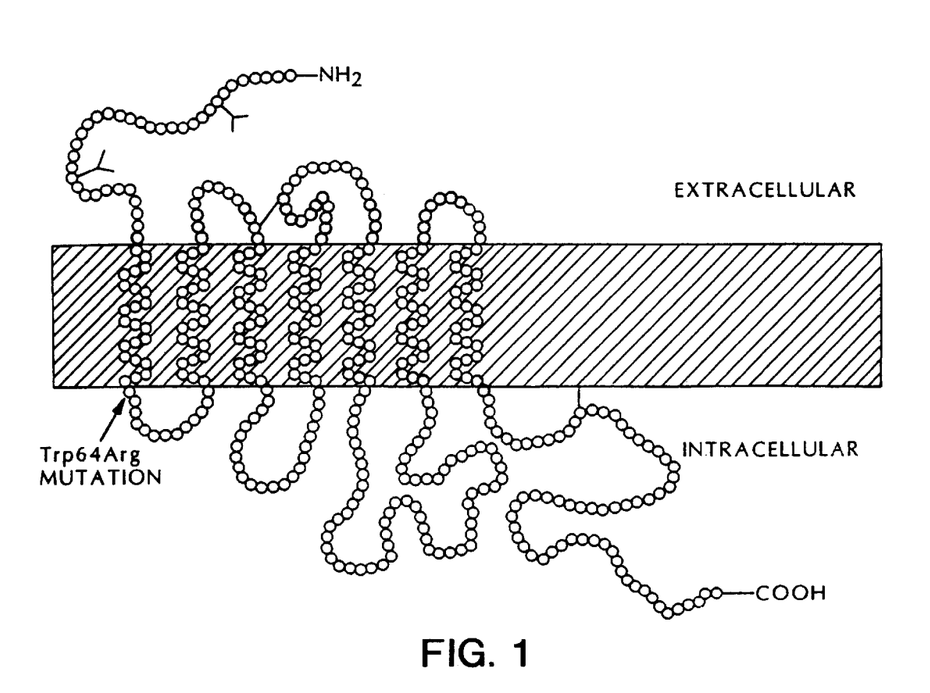
FIG. 1 shows a schematic illustration of the β3AR including the intracellular, transmembrane and extracellular domains. The mutation at codon 64 is noted by an arrow.

The non-conservative missense mutation identified in the present invention is located at the beginning of the first intracellular loop in exon 1 of the β3AR gene (FIG. 1) and results in a substitution of tryptophan (TGG) to arginine (CGG) at codon 64. This mutation causes the deletion of a BstN1 (CC↓(A/T)GG) site, which enables an amplified polymerase chain reaction (PCR) product from this region to be screened readily by digestion with this enzyme.

The human β3AR gene is located on chromosomes 8p11–p12, and encodes a 408 amino acid protein within two exons (Spronsen, et al., *Eur. J. Biochem.,* 213:1117–1124, 1993; and Granneman, et al., *Mol. Pharmacol,* 42:964–970, 1992). To examine further the potential role of inherited defects in the β3AR gene as a contributor to obesity and NIDDM, molecular scanning was performed in Pima Indians, an ethnic group with a very high prevalence of these disorders.

A nonconservative missense mutation was identified in the first intracellular loop of the β3AR(codon 64 TGGTrp→CGGArg; Trp64Arg). This missense mutation occurs with an allele frequency of 0.31 in Pima Indians, 0.13 in Mexican Americans, 0.12 in African Americans and 0.08 in Caucasian Americans. In Pimas, the mean age of onset of NIDDM was significantly earlier in subjects with the mutation (mean±SD=35.9±10.2 years in Trp64Arg homozygotes, 40.2±10.2 in Trp64Arg heterozygotes, and 40.9±10.7 in normal homozygotes; p=0.022). After adjustment for fat free mass, fat mass, and gender, Trp64Arg homozygotes (n=22) expended an average of 82 kcal/day less than normal homozygotes (n=82); Trp64Arg heterozygotes (n=106) were intermediate with an average RMR 35.7 kcal/day less than normal homozygotes (p=0.14; overall significance for regression). There was a trend towards increased body mass index (BMI) in subjects with the mutation (mean±SD= 35.2±8.0 kg/m² in Trp64Arg homozygotes, 34.1±7.9 in Trp64Arg heterozygotes, and 33.9±7.5 in normal homozygotes). Pima subjects with the Trp64Arg β3AR missense mutation have a significantly earlier onset of NIDDM, and tend to have lower RMR and increased BMI. This mutation may accelerate the onset of NIDDM by altering the balance of energy metabolism. Further, subjects who are homozygous for the mutation (particularly men and to a lesser extent women) were under-represented in the older age group suggestion association with early mortality. mRNA for the Trp64Arg β3AR was also less abundant in fat biopsies from heterozygous Pima Indians than would be expected suggesting decreased mRNA stability, decreased transcription, or both (Table 1).

TABLE 1

RELATIVE AMOUNTS OF NORMAL AND TRP64ARG β3AR mRNA IN FAT BIOPSIES FROM HETEROZYGOUS PIMA INDIANS

|  | Normal | Trp64Arg |
|---|---|---|
| Subject 1 | 1.00 | 0.43 |
| Subject 2 | 1.00 | 0.41 |
| Subject 3 | 1.00 | 0.63 |

Example 1

Materials And Methods

1. Human Subjects and Genomic DNA Isolation

The 642 subjects (390 with NIDDM and 252 without NIDDM) used for association studies were full-heritage Pima or Tohono O'odham Indians or a mixture of these two closely related tribes. All had been examined as outpatients when 35–87 years of age, and had resided in the community during the previous four years. Selection of these subjects was not based on an individual's relationship to any other subject or presence of diabetes. NIDDM was diagnosed by WHO criteria [World Health Organization. Diabetes Mellitus. Report of a WHO study group. Geneva: World Health Organization, 1985 (Technical report series 727).] Anthropometry and body composition (underwater weighing) were obtained using standard methods (Prochazka, et al., *Diabetes,* 42:514–519, 1993). Subjects used for association with RMR (obtained by indirect calorimetry in a respiratory chamber), and insulin sensitivity (obtained by hyperinsulinemic euglycemic clamp), were a separate cohort of 210 nondiabetic Pima Indians (Bogardus, et al., *N. Engl J Med,* 315:96, 1986; Prochazka, et al., *Diabetes,* 42:514–19, 1993). For estimation of allelic frequencies, β3AR genotypes were determined in Mexican Americans (n=62) from San Antonio, Texas and from African Americans (n=49) and Caucasians (n=48) from the greater Baltimore/Washington, D.C. area. Association studies were not performed in these populations because of the relatively small number of subjects, and the lack of phenotypic data.

2. Dideoxy Sequence Analysis

Single-stranded conformational polymorphism (SSCP) variants were subjected to direct dideoxy sequence analysis using asymmetric PCR to generate a single-stranded product (Shuldiner, et al., Handbook of Techniques in Endocrine Research, p. 457–486, DePablo, F., Scanes, C., eds., Academic Press, Inc., 1993). This product was subjected to conventional dideoxy sequence analysis using the Sequenase kit (U.S. Biochemicals; Cleveland, Ohio. Base changes were confirmed by sequencing opposite strands, and by restriction enzyme digestion.

3. Detection of Trp64Arg β3AR by Allele Specific Oligonucleotide Hybridization

For rapid detection of the Trp64Arg β3AR missense mutation, unlabeled PCR products from β3AR segment 4 (Table 3) were blotted in duplicate onto a nylon membrane, air dried, and UV crosslinked. Hybridization was accomplished with [$\gamma$-$^{32}$P]-ATP radio-labeled oligonucleotides corresponding to either the normal β3AR sequence [5'-C-ATCGCC$\underline{T}$GGACTCCG-3' (residues 1 through 16 of SEQ ID NO:7), (nt 183–199); Trp64 probe], or the Trp64Arg β3AR missense mutation [5'- CATCGCCTGGACTCCGA-3' (SEQ ID NO:7) (nt 183–199); Arg64 probe]. The membranes were then washed twice in 2X SSPE and 0.05% SDS at 60°C. (Trp64 probe) or 62° C. (Arg64 probe) for fifteen minutes. Autoradiography was performed at -70° C. for 4–12 hours with enhancing screens.

4. Statistical Analyses

For association studies, standard chi-square or Fisher exact tests (if expected cell size was <5) were performed based on genotype using standard statistical packages. For analysis of quantitative traits, Student's unpaired t-test, ANOVA, or ANCOVA models were used, and when possible, information on covariates were included in the linear model. Data are expressed as the mean±standard deviation.

5. Polymerase Chain Reaction (PCR) Amplification

Genomic DNA (0.1 μg) extracted from blood cells of the patient was amplified in a final volume of 50 μl containing PCR buffer (50 mM KCl, 10 mM Tris-HCl, pH 8.3 at 25° C., 2.5 mM MgCl$_2$, and 0.01 mg/ml gelatin) 20 μM each dNTP, 0.5 μM each primer (upstream 5'CGCCCAATACCGCCAA-CAC3'; SEQ ID NO:3 and downstream 5'CCACCAG-GAGTCCCATCACC3'; SEQ ID NO:4), 10% DMSO, and 1 unit of Taq polymerase (Boehringer Mannheim, Indianapolis, Ind.). Thirty-five cycles were performed, each consisting of denaturation (94° C.; 1 min), annealing (57° C.; 1 min), and extension (72° C.; 1 min), except during the first cycle in which the denaturing time was increased to 5 minutes, and during the last cycle in which the extension time was increased to 10 minutes. The yield and purity of the 210 bp PCR product was determined by electrophoresis on a composite gel consisting of 1% agarose/2% NuSieve GTG (FMC Bioproducts; Rockland, Me.).

6. Allele Specific Oligonucleotide Hybridization

For genotyping of large numbers of subjects, an allele specific oligonucleotide (ASO) hybridization asssay for rapid detection of the Trp64Arg β3AR missense mutation was used. Two oligonucleotide probes were designed, each 17 bases in length—one with the Trp64β3AR sequence (5'CATCGCC$\underline{T}$GGACTCCGA3'; SEQ ID NO:7), and the second differing by a single nucleotide with the Arg$^{64}$ β3AR sequence (5'CATCGCC$\underline{C}$GGACTCCGA3'; SEQ ID NO:8), and radiolabeled with $\gamma$-[$^{32}$P]-ATP by polynucleotide kinase. Hybridization and wash conditions were optimized so that each probe would recognize only its exact complementary sequence.

The PCR product described above was blotted onto a nylon membrane (Nytran; Schleicher and Schuell; Keen, N. H.). After UV crosslinking, the membrane was cut into equal halves, and each half was hybridized with a [$^{32}$P]- radiolabeled oligonucleotide probe whose sequence is specific for either the Trp64 or Arg64 β3AR sequence (see above). Hybridization was accomplished in 5× SSPE, 5× Denhardt's solution, 1% SDS, 1 mg/ml salmon sperm DNA, and 1×10$^6$ CPM/ml [$^{32}$P]-radiolabeled oligonucleotide probe at 42° C. for 6 to 18 hours. The membranes were washed twice in 2× SSPE and 0.05% SDS at 60° C. (Trp64 β3AR probe) or 62° C. (Arg64 β3AR probe) for fifteen minutes. Autoradiography was performed at -70° C. for 4–12 hours with enhancing screens. Trp64 β3AR homozygous and Arg64 β3AR homozygous controls were included in each assay to assure that hybridization was specific. The method may also be adapted for nonradioisotopic detection using routine methods.

7. Restriction Enzyme Digestion with BstN1

Since the Trp$^{64}$β3AR mutation eradicates a BstN1 site, digestion with this enzyme may be used diagnostically to detect the mutation. Ten microliters (approximately 200 ng) of the PCR product described above was added directly to a restriction enzyme digestion mixture in a final volume of 20 μl containing digestion buffer and 1–5 U of BstN1 (Boehringer Mannheim). After incubation for 1–2 hours at 60° C., the products were electrophoresed on a composite gel consisting of 3% NuSieve GTG, and 1% agarose. Table 2 shows the predicted sizes of the digestion products for each of the three β3AR genotypes.

TABLE 2

PREDICTED SIZES OF DIAGNOSTIC BstN1 DIGEST TO DETECT THE TRP64ARG β3AR MUTATION
size of fragment from BstN1 digest (bp)

| NN | NM | MM |
|---|---|---|
| — | 158 | 158 |
| 97 | 97 | — |
| 61 | 61 | — |
| 29 | 29 | 29 |
| 15 | 15 | 15 |
| 8 | 8 | 8 |

NN = nominal homozygote;
NM = heterozygote;
MM = Trp64Arg homozygote

Example 2

Single-Stranded Conformational Polymorphism (SSCP) Analysis Of The β3AR Gene

Figure 2A:
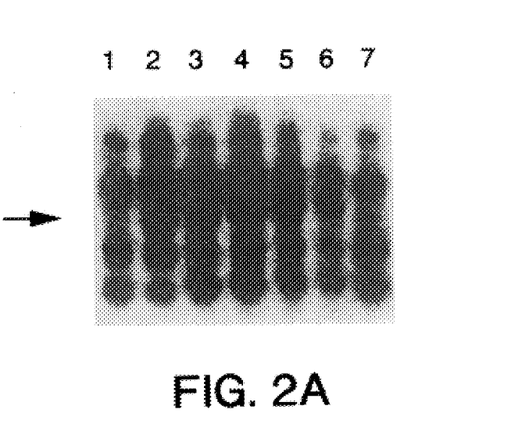
Figure 2B:
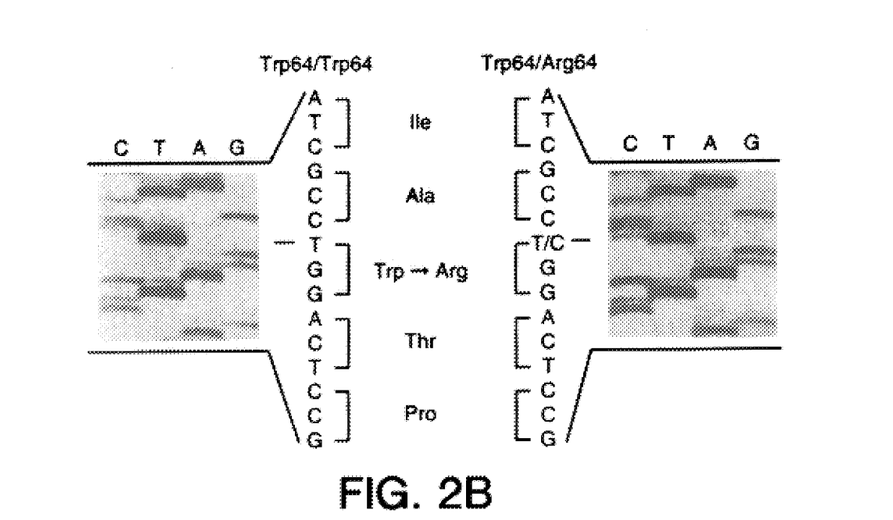

The β3AR gene was initially screened for variation in 10 unrelated Pima Indians with obesity and NIDDM. SSCP analysis performed on 10 overlapping PCR products from each of the probands revealed two variant patterns in the coding region. Dideoxy sequence analysis of the variant in segment 5 (present in 2 of 10 Pimas) revealed a C→T change at nucleotide position 381 which did not predict any change in the amino acid sequence (codon 127 AC $\underline{C}^{Thr}$–AC$\underline{T}^{Thr}$). Direct dideoxy sequence analysis of the variant in segment 4 (present in 5 of 10 Pimas) revealed a heterozygous pattern with a T→C change at nucleotide position 190 (FIG. 2). This base change predicted a nonconservative substitution of tryptophan (T̲GG) to arginine ( CGG) at position 64 (Trp64Arg), an amino acid at the beginning of the first intracellular loop of this seven membrane spanning, G protein linked receptor. This base change was confirmed by restriction enzyme digestion with BstN1. To screen for mutations that may have been missed by SSCP analysis, the entire coding region of the β3AR gene was sequenced directly in two additional Pima Indians with NIDDM. No new base changes were identified.

Example 3

Figure 3:
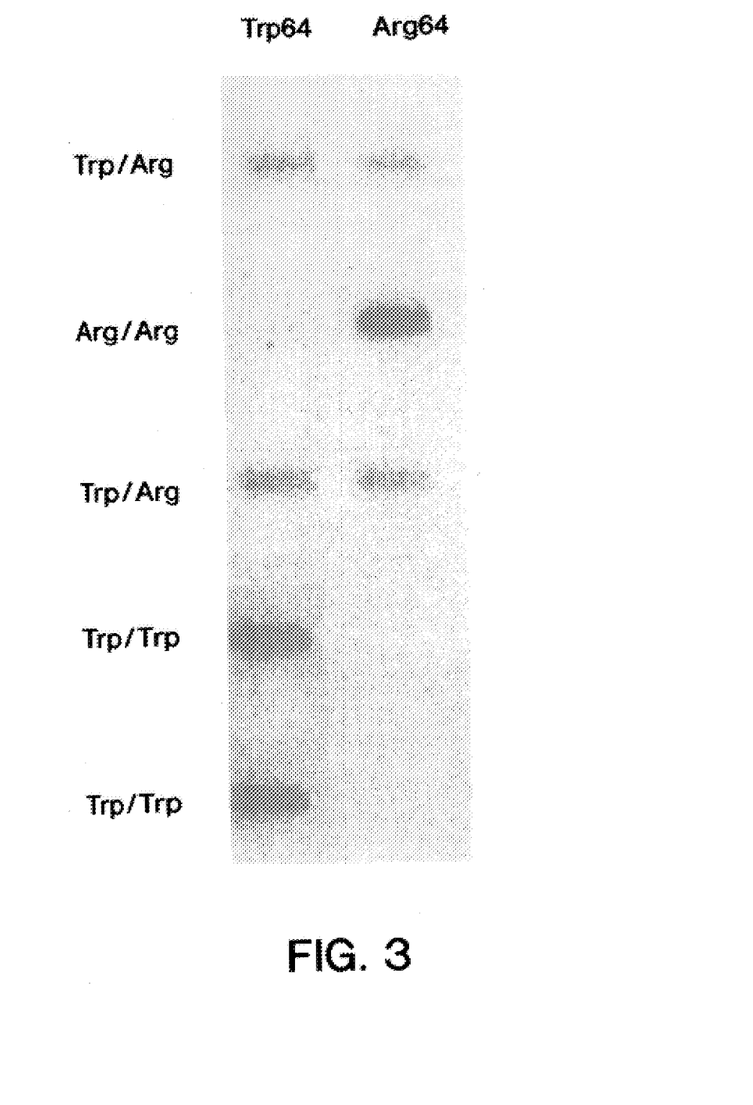
FIG. 3 shows allele specific oligonucleotide (ASO) hybridization to detect the Trp64Arg and normal β3AR. PCR segment 4 from Pima Indians were subjected to slot blot analysis in duplicate with oligonucleotide probes that recognize specifically the Trp64Arg mutation ($Arg^{64}$ probe) or the normal β3AR sequence ($Trp^{64}$ probe). Normal homozygotes (Trp/Trp), Trp64Arg β3AR heterozygotes (Trp/Arg), and Trp64Arg β3AR homozygotes (Arg/Arg) could be detected rapidly.

Allele Frequencies Of The Trp64Arg β3AR Missense Mutation In Pima Indians And Mexican, African, And Caucasian Americans Genomic DNA from 642 unrelated Pima Indians (390 subjects with NIDDM, and 252 without NIDDM) between the ages of 35 and 87 was subjected to genotyping for the Trp64Arg β3AR missense mutation using an allele specific oligonucleotide (ASO) hybridization assay (FIG. 3). The Trp64Arg β3AR allele had a high prevalence among Pima Indians with a frequency of 0.31 (n=1284 alleles). Nine per cent were homozygous for the Trp64Arg mutation, 45% were heterozygous, and 46% lacked the mutation. When genotypes were analyzed by age and gender, there was a statistically significant under-representation of subjects homozygous for the Trp64Arg missense mutation in the older men (Table 4) (p=0.015).

The Trp64Arg β3AR missense mutation is also present in Mexican Americans (allele frequency 0.013; n=124 alleles), and African Americans (allele frequency 0.12; n=98 alleles), as well as Caucasian Americans (allele frequency 0.08; n=96 alleles).

Example 4

Trp64Arg β3AR AND NIDDM

The overall prevalence of NIDDM was slightly, but not significantly higher in subjects who were homozygous for the Trp64Arg β3AR missense mutation (Table 5). However, Trp64Arg β3AR homozygotes had an average age of onset of NIDDM that was significantly earlier than normal homozygotes and Trp64Arg β3AR heterozygotes (35.9±10.2 years in Trp64Arg β3AR homozygotes, 40.2±10.2 in Trp64Arg β3AR heterozygotes, and 40.9±10.7 in normal homozygotes; p=0.022) (Table 5). Early onset NIDDM, defined as onset prior to the age of 25, was approximately 3-fold more frequent in Trp64Arg β3AR homozygotes than normal homozygoses or Trp64Arg β3AR heterozygotes (Table 5).

Example 5

Resting Metabolic Rate And Obesity

There was a trend toward a lower resting metabolic rate in subjects with the Trp64Arg β3AR missense mutation (Table 5). In Trp64Arg β3AR homozygotes, the average resting metabolic rate was 1769±290 kcal/day, while in normal homozygotes the average resting metabolic rate was 1831±345 kcal/day. After adjustment for fat free mass, fat mass and gender, known covariates of resting metabolic rate, Trp64Arg β3AR homozygotes (n=22) expended an average of 82 kcal/day less than normal β3AR homozygotes (n=82); Trp64Arg heterozygotes (n=106) were intermediate between the two with an average resting metabolic rate 35.7 kcal/day less than normal β3AR homozygotes (p=0.14; overall significance for regression).

Further, there was a trend towards increased body mass index (BMI) in subjects with the Trp64Arg missense mutation (mean±SD=35.2±8.0 kg/m$^2$ in Trp64Arg β3AR homozygotes, 34.1±7.9 kg/m$^2$ in Trp64Arg β3AR heterozygotes, and 33.9±7.5 kg/m$^2$ in normal homozygotes) (Table 5). No significant associations or trends were found with waist to hip ratio or with insulin sensitivity as measured by euglycemic hyperinsulinemic clamp, glucose, or insulin levels during an oral glucose tolerance test.

TABLE 3

PRIMER SEQUENCES USED FOR PCR AMPLIFICATION OF THE β3AR GENE

| Fragment | Sequence (5'→3') | Nucleotide Position† | Predicted Size |
|---|---|---|---|
| 1 UP | GAAAGGGGACAGATCTCACCAA (SEQ ID NO:9) | −646—625 | 323 |
| 1 DOWN | TTCCTCTGCCACCATCTGT (SEQ ID NO:10) | −341—323 | |
| 2 UP | CCAGGGAGTGCTATGCTGAG (SEQ ID NO:11) | −389—370 | 229 |
| 2 DOWN | AACTCCCTCGGTGCCACCGCTCTT (SEQ ID NO:12) | −183—160 | |
| 3 UP | TTAAGCGTCGCTACTCCTCC (SEQ ID NO:13) | −206—187 | 246 |
| 3 DOWN | GGCCATGGGGCAAGAGAGCTGTT (SEQ ID NO:14) | 22–40 | |
| 4 UP | TTCCTTCTTTCCCTACCGCCC (SEQ ID NO:15) | −37—17 | 367 |
| 4 DOWN | GCAGCCAGTGGCGCCCAACGG (SEQ ID NO:16) | 310–330 | |
| 5 UP | ACCTTGGCGCTGACTGGCCAC (SEQ ID NO:17) | 285–306 | 310 |
| 5 DOWN | CACGTAGGGCATGTTGGAGGC (SEQ ID NO:18) | 575–595 | |
| 6 UP | CAGTGGTGGCGCGTAGGGGCC (SEQ ID NO:19) | 526–546 | 264 |
| 6 DOWN | TTCGGGCGGAGCGCACGTCCC (SEQ ID NO:20) | 770–790 | |
| 7 UP | GGCCGCTTTCCGCCCGAGGAG (SEQ ID NO:21) | 707–727 | 266 |
| 7 DOWN | CAGGGCAAGGAAAGCCGGGCC (SEQ ID NO:22) | 953–973 | |
| 8 UP | ATGGGCACCTTCACTCTCTGCT (SEQ ID NO:23) | 872–892 | 321 |
| 8 DOWN | TTACCTACCCGTCGAGCCGTTG (SEQ ID NO:24) | 1173–1193 | |
| 9 UP | GAACTGGCTAGGTTATGCCAA (SEQ ID NO:25) | 973–993 | 279 |
| 9 DOWN | CCACGGACACATCGCATGCTT (SEQ ID NO:26) | 1884–1094* | |
| 10 UP | TGCACCTGTTGCTCCTTTCAC (SEQ ID NO: 27) | 2814–2834* | 102 |
| 10 DOWN | AGAGTTGTTGCTTCTTGTCCT (SEQ ID NO:28) | 2895–2916* | |

† Numbering based on that of Liggett, et al., DNA Sequence 2:61–63, 1992, and Muzzin, et al., J Biol. Chem., 266:24053–24058, 1991.
*Numbering based on that of Spronsen, et al., Eur. J Biochem., 213:1117–1124, 1993.
UP = upstream (sense); DOWN downstream (antisense)

TABLE 4

FREQUENCY OF HOMOZYGOTES FOR THE Trp64Arg β3AR GENE MUTATION

| Age | Men[†] | Trp64Arg Homozygotes (%) Women | All[¥] |
|---|---|---|---|
| 35–44 | 10/77 (13.0%) | 17/158 (10.8%) | 27/235 (11.5%) |
| >45 | 7/162 (4.3%) | 23/245 (9.4%) | 30/407 (7.4%) |

[†]p = 0.015 for difference between age groups in men
[¥]p = 0.08 for difference between age groups in men and women combined

TABLE 5

CHARACTERISTICS OF PIMA SUBJECTS BY β3AR GENOTYPE

| | Trp64Arg β3AR Homozygotes | Trp64Arg β3AR Heterozygotes | Normal β3AR Homozygotes |
|---|---|---|---|
| Population Sample | 57 | 290 | 295 |
| Male/Female | 17/40 | 105/185 | 117/178 |
| Mean Age (years) | 48.1 ± 10.5 | 50.5 ± 10.3 | 50.7 ± 10.7 |
| Prevelance of Diabetes, Any Age (%) | 41 (72%) | 173 (60%) | 176 (60%) |
| Mean Age of NIDDM Onset (years) | 35.9 ± 10.2* | 40.2 ± 10.2 | 40.9 ± 10.7 |
| Diabetes Onset Prior to Age 25 (%) | 5 (9%)[†] | 10 (3%) | 9 (3%) |
| BMI (kg/m$^2$) | 35.2 ± 8.0 | 34.1 ± 7.9 | 33.9 ± 7.5 |
| Difference in Adjusted Resting Metabolic Rate (kcal/day)[¥] | −82 [n = 22] | −35.7 [n = 106] | 0 [n = 82] |

*Trp64Arg β3AR homozygotes were significantly different from Trp64Arg β3AR heterozygotes and normal β3AR homozygotes by analysis of variance (p = 0.022).
[†]p = 0.05 Trp64Arg β3AR homozygotes compared to Trp64Arg β3AR heterozygotes and normal β3AR homozygotes combined (prevalence ratio between these two groups = 2.7; 95% confidence limits 1.1–6.8).
[¥]Subjects were unrelated and nondiabetic and represent a separate cohort (see Example ). Data was adjusted for fat free mass, fat mass and gender; p = 0.14 for overall regression.

Although the invention has been described with reference to the presently preferred embodiment, it should be understood that various modifications can be made without departing from the spirit of the invention. Accordingly, the invention is limited only by the following claims.

---

We claim:

1. An isolated polypeptide having an amino acid sequence of a β3-adrenergic receptor having a substitution of tryptophan at amino acid residue 64 with arginine and wherein the substituted receptor is associated with having or at risk of having an increased likelihood for developing Type II diabetes mellitus and/or obesity.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

GTGTTGGCCG TATTGGGCG        19

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

GGTGATGGGA CTCCTGGTGG        20

( 2 ) INFORMATION FOR SEQ ID NO:3:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:3:

CGCCCAATAC CGCCAACAC                 19

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

CCACCAGGAG TCCCATCACC                 20

( 2 ) INFORMATION FOR SEQ ID NO:5:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

TCGGAGTCCA GGCGATG                    17

( 2 ) INFORMATION FOR SEQ ID NO:6:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

TCGGAGTCCG GGCGATG                    17

( 2 ) INFORMATION FOR SEQ ID NO:7:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

CATCGCCTGG ACTCCGA                    17

( 2 ) INFORMATION FOR SEQ ID NO:8:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear (i i) MOLECULE TYPE: DNA (genomic)

(x i) SEQUENCE DESCRIPTION: SEQ ID NO:8:

CATCGCCCGG ACTCCGA                                                             17

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (i i) MOLECULE TYPE: DNA (genomic)

(x i) SEQUENCE DESCRIPTION: SEQ ID NO:9:

GAAAGGGGAC AGATCTCACC AA                                                       22

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (i i) MOLECULE TYPE: DNA (genomic)

(x i) SEQUENCE DESCRIPTION: SEQ ID NO:10:

TTCCTCTGCC ACCATCTGT                                                           19

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (i i) MOLECULE TYPE: DNA (genomic)

(x i) SEQUENCE DESCRIPTION: SEQ ID NO:11:

CCAGGGAGTG CTATGCTGAG                                                          20

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (i i) MOLECULE TYPE: DNA (genomic)

(x i) SEQUENCE DESCRIPTION: SEQ ID NO:12:

AACTCCCTCG GTGCCACCGC TCTT                                                     24

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (i i) MOLECULE TYPE: DNA (genomic)

(x i) SEQUENCE DESCRIPTION: SEQ ID NO:13:

TTAAGCGTCG CTACTCCTCC 20

(2) INFORMATION FOR SEQ ID NO:14:

(i) SEQUENCE CHARACTERISTICS:
  (A) LENGTH: 23 base pairs
  (B) TYPE: nucleic acid
  (C) STRANDEDNESS: single
  (D) TOPOLOGY: linear  (ii) MOLECULE TYPE: DNA (genomic)

(xi) SEQUENCE DESCRIPTION: SEQ ID NO:14:

GGCCATGGGG CAAGAGAGCT GTT 23

(2) INFORMATION FOR SEQ ID NO:15:

(i) SEQUENCE CHARACTERISTICS:
  (A) LENGTH: 21 base pairs
  (B) TYPE: nucleic acid
  (C) STRANDEDNESS: single
  (D) TOPOLOGY: linear  (ii) MOLECULE TYPE: DNA (genomic)

(xi) SEQUENCE DESCRIPTION: SEQ ID NO:15:

TTCCTTCTTT CCCTACCGCC C 21

(2) INFORMATION FOR SEQ ID NO:16:

(i) SEQUENCE CHARACTERISTICS:
  (A) LENGTH: 21 base pairs
  (B) TYPE: nucleic acid
  (C) STRANDEDNESS: single
  (D) TOPOLOGY: linear  (ii) MOLECULE TYPE: DNA (genomic)

(xi) SEQUENCE DESCRIPTION: SEQ ID NO:16:

GCAGCCAGTG GCGCCCAACG G 21

(2) INFORMATION FOR SEQ ID NO:17:

(i) SEQUENCE CHARACTERISTICS:
  (A) LENGTH: 21 base pairs
  (B) TYPE: nucleic acid
  (C) STRANDEDNESS: single
  (D) TOPOLOGY: linear  (ii) MOLECULE TYPE: DNA (genomic)

(xi) SEQUENCE DESCRIPTION: SEQ ID NO:17:

ACCTTGGCGC TGACTGGCCA C 21

(2) INFORMATION FOR SEQ ID NO:18:

(i) SEQUENCE CHARACTERISTICS:
  (A) LENGTH: 21 base pairs
  (B) TYPE: nucleic acid
  (C) STRANDEDNESS: single
  (D) TOPOLOGY: linear  (ii) MOLECULE TYPE: DNA (genomic)

(xi) SEQUENCE DESCRIPTION: SEQ ID NO:18:

CACGTAGGGC ATGTTGGAGG C 21

(2) INFORMATION FOR SEQ ID NO:19:

( i ) SEQUENCE CHARACTERISTICS:
 ( A ) LENGTH: 21 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:19:

CAGTGGTGGC GCGTAGGGGC C                             21

( 2 ) INFORMATION FOR SEQ ID NO:20:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:20:

TTCGGGCGGA GCGCACGTCC C                             21

( 2 ) INFORMATION FOR SEQ ID NO:21:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:21:

GGCCGCTTTC CGCCCGAGGA G                             21

( 2 ) INFORMATION FOR SEQ ID NO:22:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:22:

CAGGGCAAGG AAAGCCGGGC C                             21

( 2 ) INFORMATION FOR SEQ ID NO:23:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:23:

ATGGGCACCT TCACTCTCTG CT                            22

( 2 ) INFORMATION FOR SEQ ID NO:24:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear (i i) MOLECULE TYPE: DNA (genomic)

(x i) SEQUENCE DESCRIPTION: SEQ ID NO:24:

TTACCTACCC GTCGAGCCGT TG  22

(2) INFORMATION FOR SEQ ID NO:25:

(i) SEQUENCE CHARACTERISTICS:
  (A) LENGTH: 21 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:25:

GAACTGGCTA GGTTATGCCA A  21

(2) INFORMATION FOR SEQ ID NO:26:

(i) SEQUENCE CHARACTERISTICS:
  (A) LENGTH: 21 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:26:

CCACGGACAC ATCGCATGCT T  21

(2) INFORMATION FOR SEQ ID NO:27:

(i) SEQUENCE CHARACTERISTICS:
  (A) LENGTH: 21 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:27:

TGCACCTGTT GCTCCTTTCA C  21

(2) INFORMATION FOR SEQ ID NO:28:

(i) SEQUENCE CHARACTERISTICS:
  (A) LENGTH: 21 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:28:

AGAGTTGTTG CTTCTTGTCC T  21